(12) United States Patent
Hindson

(10) Patent No.: US 8,709,762 B2
(45) Date of Patent: Apr. 29, 2014

(54) SYSTEM FOR HOT-START AMPLIFICATION VIA A MULTIPLE EMULSION

(75) Inventor: Benjamin J. Hindson, Livermore, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 147 days.

(21) Appl. No.: 13/039,233

(22) Filed: Mar. 2, 2011

(65) Prior Publication Data
US 2011/0217736 A1 Sep. 8, 2011

Related U.S. Application Data

(60) Provisional application No. 61/309,837, filed on Mar. 2, 2010.

(51) Int. Cl.
*C12N 9/12* (2006.01)
*C12P 19/34* (2006.01)

(52) U.S. Cl.
USPC ............. 435/91.2; 134/14; 134/561; 435/194

(58) Field of Classification Search
USPC ................................. 435/91.2, 194
See application file for complete search history.

(56) References Cited

U.S. PATENT DOCUMENTS

| | | | |
|---|---|---|---|
| 3,575,220 A | 4/1971 | Davis et al. | |
| 4,051,025 A | 9/1977 | Ito | |
| 4,201,691 A | 5/1980 | Asher et al. | |
| 4,283,262 A | 8/1981 | Cormier et al. | |
| 4,348,111 A | 9/1982 | Goulas et al. | |
| 4,636,075 A | 1/1987 | Knollenberg | |
| 4,948,961 A | 8/1990 | Hillman et al. | |
| 5,055,390 A | 10/1991 | Weaver et al. | |
| 5,176,203 A | 1/1993 | Larzul | |
| 5,225,332 A | 7/1993 | Weaver et al. | |
| 5,270,183 A | 12/1993 | Corbett et al. | |
| 5,314,809 A | 5/1994 | Erlich et al. | |
| 5,344,930 A | 9/1994 | Riess et al. | |
| 5,422,277 A | 6/1995 | Connelly et al. | |
| 5,538,667 A | 7/1996 | Hill et al. | |
| 5,555,191 A | 9/1996 | Hripcsak | |
| 5,585,069 A | 12/1996 | Zanzucchi et al. | |
| 5,587,128 A | 12/1996 | Wilding et al. | |
| 5,602,756 A | 2/1997 | Atwood et al. | |
| 5,720,923 A | 2/1998 | Haff et al. | |
| 5,736,314 A | 4/1998 | Hayes et al. | |
| 5,779,977 A | 7/1998 | Haff et al. | |
| 5,827,480 A | 10/1998 | Haff et al. | |
| 5,856,174 A | 1/1999 | Lipshutz et al. | |
| 5,912,945 A | 6/1999 | Da Silva et al. | |
| 5,928,907 A | 7/1999 | Woudenberg et al. | |
| 5,945,334 A | 8/1999 | Besemer et al. | |
| 5,972,716 A | 10/1999 | Ragusa et al. | |
| 5,980,936 A | 11/1999 | Krafft et al. | |
| 5,994,056 A | 11/1999 | Higuchi | |
| 6,033,880 A | 3/2000 | Haff et al. | |
| 6,042,709 A | 3/2000 | Parce et al. | |
| 6,057,149 A | 5/2000 | Burns et al. | |
| 6,126,899 A | 10/2000 | Woudenberg et al. | |
| 6,130,098 A | 10/2000 | Handique et al. | |
| 6,143,496 A | 11/2000 | Brown et al. | |
| 6,146,103 A | 11/2000 | Lee et al. | |
| 6,171,785 B1 | 1/2001 | Higuchi | |
| 6,175,669 B1 | 1/2001 | Colston et al. | |
| 6,176,609 B1 | 1/2001 | Cleveland et al. | |
| 6,177,479 B1 | 1/2001 | Nakajima et al. | |
| 6,210,879 B1 | 4/2001 | Meloni et al. | |
| 6,258,569 B1 | 7/2001 | Livak et al. | |
| 6,281,254 B1 | 8/2001 | Nakajima et al. | |
| 6,303,343 B1 | 10/2001 | Kopf-Sill | |
| 6,357,907 B1 | 3/2002 | Cleveland et al. | |
| 6,384,915 B1 | 5/2002 | Everett et al. | |
| 6,391,559 B1 | 5/2002 | Brown et al. | |
| 6,440,706 B1 | 8/2002 | Vogelstein et al. | |
| 6,466,713 B2 | 10/2002 | Everett et al. | |
| 6,488,895 B1 | 12/2002 | Kennedy | |
| 6,489,103 B1 | 12/2002 | Griffiths et al. | |
| 6,494,104 B2 | 12/2002 | Kawakita et al. | |
| 6,509,085 B1 | 1/2003 | Kennedy | |
| 6,521,427 B1 | 2/2003 | Evans | |
| 6,524,456 B1 | 2/2003 | Ramsey et al. | |
| 6,540,895 B1 | 4/2003 | Spence et al. | |

(Continued)

FOREIGN PATENT DOCUMENTS

| EP | 1 522 582 A2 | 4/2005 |
|---|---|---|
| EP | 1 522 582 B1 | 4/2007 |

(Continued)

OTHER PUBLICATIONS

Young, Lee W., Authorized officer, International Searching Authority, International Search Report, PCT Application No. PCT/US 201046519; mail date: Oct. 15, 2010.

(Continued)

*Primary Examiner* — Kenneth R. Horlick
*Assistant Examiner* — Olayinka Oyeyemi
(74) *Attorney, Agent, or Firm* — Kolisch Hartwell, P.C.

(57) ABSTRACT

System, including methods, apparatus, compositions, and kits, for making and using compound droplets of a multiple emulsion to supply an amplification reagent, such as a heat-stable DNA polymerase or DNA ligase, to an aqueous phase in which the compound droplets are disposed. The compound droplets may be induced to supply the amplification reagent by heating the multiple emulsion, to achieve hot-start amplification.

14 Claims, 2 Drawing Sheets

(56) References Cited

U.S. PATENT DOCUMENTS

| | | |
|---|---|---|
| 6,551,841 B1 | 4/2003 | Wilding et al. |
| 6,558,916 B2 | 5/2003 | Veerapandian et al. |
| 6,575,188 B2 | 6/2003 | Parunak |
| 6,602,472 B1 | 8/2003 | Zimmermann et al. |
| 6,620,625 B2 | 9/2003 | Wolk et al. |
| 6,637,463 B1 | 10/2003 | Lei et al. |
| 6,638,749 B1 | 10/2003 | Beckman et al. |
| 6,660,367 B1 | 12/2003 | Yang et al. |
| 6,663,619 B2 | 12/2003 | Odrich et al. |
| 6,664,044 B1 | 12/2003 | Sato |
| 6,670,153 B2 | 12/2003 | Stern |
| 6,753,147 B2 | 6/2004 | Vogelstein et al. |
| 6,767,706 B2 | 7/2004 | Quake et al. |
| 6,773,566 B2 | 8/2004 | Shenderov |
| 6,808,882 B2 | 10/2004 | Griffiths et al. |
| 6,814,934 B1 | 11/2004 | Higuchi |
| 6,833,242 B2 | 12/2004 | Quake et al. |
| 6,900,021 B1 | 5/2005 | Harrison et al. |
| 6,905,885 B2 | 6/2005 | Colston et al. |
| 6,949,176 B2 | 9/2005 | Vacca et al. |
| 6,960,437 B2 | 11/2005 | Enzelberger et al. |
| 6,964,846 B1 | 11/2005 | Shuber |
| 7,010,391 B2 | 3/2006 | Handique et al. |
| 7,041,481 B2 | 5/2006 | Anderson et al. |
| 7,052,244 B2 | 5/2006 | Fouillet et al. |
| 7,081,336 B2 | 7/2006 | Bao et al. |
| 7,091,048 B2 | 8/2006 | Parce et al. |
| 7,094,379 B2 | 8/2006 | Fouillet et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,141,537 B2 | 11/2006 | Audenaert et al. |
| 7,192,557 B2 | 3/2007 | Wu et al. |
| 7,198,897 B2 | 4/2007 | Wangh et al. |
| 7,238,268 B2 | 7/2007 | Ramsey et al. |
| 7,244,567 B2 | 7/2007 | Chen et al. |
| 7,252,943 B2 | 8/2007 | Griffiths et al. |
| 7,268,167 B2 | 9/2007 | Higuchi et al. |
| 7,268,179 B2 | 9/2007 | Brown |
| 7,270,786 B2 | 9/2007 | Parunak et al. |
| 7,279,146 B2 | 10/2007 | Nassef et al. |
| 7,294,468 B2 | 11/2007 | Bell et al. |
| 7,294,503 B2 | 11/2007 | Quake et al. |
| 7,306,929 B2 | 12/2007 | Ignatov et al. |
| 7,312,085 B2 | 12/2007 | Chou et al. |
| 7,323,305 B2 | 1/2008 | Leamon et al. |
| 7,368,233 B2 | 5/2008 | Shuber et al. |
| 7,375,140 B2 | 5/2008 | Higuchi et al. |
| 7,423,751 B2 | 9/2008 | Hairston et al. |
| 7,429,467 B2 | 9/2008 | Holliger et al. |
| 7,567,596 B2 | 7/2009 | Dantus et al. |
| 7,579,172 B2 | 8/2009 | Cho et al. |
| 7,595,195 B2 | 9/2009 | Lee et al. |
| 7,622,280 B2 | 11/2009 | Holliger et al. |
| 7,629,123 B2 | 12/2009 | Millonig et al. |
| 7,776,927 B2 | 8/2010 | Chu et al. |
| 7,807,920 B2 | 10/2010 | Linke et al. |
| 7,842,457 B2 | 11/2010 | Berka et al. |
| 8,399,198 B2 | 3/2013 | Hiddessen et al. |
| 2001/0046701 A1 | 11/2001 | Schulte et al. |
| 2002/0021866 A1 | 2/2002 | Everett et al. |
| 2002/0022261 A1 | 2/2002 | Anderson et al. |
| 2002/0060156 A1 | 5/2002 | Mathies et al. |
| 2002/0068357 A1 | 6/2002 | Mathies et al. |
| 2002/0093655 A1 | 7/2002 | Everett et al. |
| 2002/0141903 A1 | 10/2002 | Parunak et al. |
| 2002/0142483 A1 | 10/2002 | Yao et al. |
| 2002/0151040 A1 | 10/2002 | O'Keefe et al. |
| 2002/0164820 A1 | 11/2002 | Brown |
| 2002/0195586 A1 | 12/2002 | Auslander et al. |
| 2003/0001121 A1 | 1/2003 | Hochstein |
| 2003/0003054 A1 | 1/2003 | McDonald et al. |
| 2003/0003441 A1 | 1/2003 | Colston et al. |
| 2003/0008308 A1 | 1/2003 | Enzelberger et al. |
| 2003/0027150 A1 | 2/2003 | Katz |
| 2003/0027244 A1 | 2/2003 | Colston et al. |
| 2003/0027352 A1 | 2/2003 | Hooper et al. |
| 2003/0032172 A1 | 2/2003 | Colston, Jr. et al. |
| 2003/0049659 A1 | 3/2003 | Lapidus et al. |
| 2003/0087300 A1 | 5/2003 | Knapp et al. |
| 2003/0170698 A1 | 9/2003 | Gascoyne et al. |
| 2003/0180765 A1 | 9/2003 | Traverso et al. |
| 2003/0204130 A1 | 10/2003 | Colston, Jr. et al. |
| 2004/0007463 A1 | 1/2004 | Ramsey et al. |
| 2004/0038385 A1 | 2/2004 | Langlois et al. |
| 2004/0067493 A1 | 4/2004 | Matsuzaki et al. |
| 2004/0068019 A1 | 4/2004 | Higuchi et al. |
| 2004/0074849 A1 | 4/2004 | Brown et al. |
| 2004/0171055 A1 | 9/2004 | Brown |
| 2004/0180346 A1 | 9/2004 | Anderson et al. |
| 2004/0208792 A1 | 10/2004 | Linton et al. |
| 2005/0036920 A1 | 2/2005 | Gilbert |
| 2005/0042639 A1 | 2/2005 | Knapp et al. |
| 2005/0064460 A1 | 3/2005 | Holliger et al. |
| 2005/0079510 A1 | 4/2005 | Berka et al. |
| 2005/0112541 A1 | 5/2005 | Durack et al. |
| 2005/0172476 A1 | 8/2005 | Stone et al. |
| 2005/0202429 A1 | 9/2005 | Trau et al. |
| 2005/0221279 A1 | 10/2005 | Carter et al. |
| 2005/0221373 A1 | 10/2005 | Enzelberger et al. |
| 2005/0227264 A1 | 10/2005 | Nobile et al. |
| 2005/0239192 A1 | 10/2005 | Nasarabadi et al. |
| 2005/0277125 A1 | 12/2005 | Benn et al. |
| 2005/0282206 A1 | 12/2005 | Corbett et al. |
| 2006/0014187 A1 | 1/2006 | Li et al. |
| 2006/0057599 A1 | 3/2006 | Dzenitis et al. |
| 2006/0077755 A1 | 4/2006 | Higuchi et al. |
| 2006/0079583 A1 | 4/2006 | Higuchi et al. |
| 2006/0079584 A1 | 4/2006 | Higuchi et al. |
| 2006/0079585 A1 | 4/2006 | Higuchi et al. |
| 2006/0094108 A1 | 5/2006 | Yoder et al. |
| 2006/0106208 A1 | 5/2006 | Nochumson et al. |
| 2006/0188463 A1 | 8/2006 | Kim et al. |
| 2007/0003442 A1 | 1/2007 | Link et al. |
| 2007/0010974 A1 | 1/2007 | Nicoli et al. |
| 2007/0048756 A1 | 3/2007 | Mei et al. |
| 2007/0109542 A1 | 5/2007 | Tracy et al. |
| 2007/0166200 A1 | 7/2007 | Zhou et al. |
| 2007/0195127 A1 | 8/2007 | Ahn et al. |
| 2007/0196397 A1 | 8/2007 | Torii et al. |
| 2007/0202525 A1 | 8/2007 | Quake et al. |
| 2007/0231393 A1* | 10/2007 | Ritter et al. .................. 424/489 |
| 2007/0242111 A1 | 10/2007 | Pamula et al. |
| 2007/0248956 A1 | 10/2007 | Buxbaum et al. |
| 2007/0258083 A1 | 11/2007 | Heppell et al. |
| 2007/0275415 A1 | 11/2007 | Srinivasan et al. |
| 2008/0003142 A1 | 1/2008 | Link et al. |
| 2008/0014589 A1* | 1/2008 | Link et al. ..................... 435/6 |
| 2008/0038810 A1* | 2/2008 | Pollack et al. ............ 435/283.1 |
| 2008/0070862 A1 | 3/2008 | Laster et al. |
| 2008/0090244 A1 | 4/2008 | Knapp et al. |
| 2008/0138815 A1 | 6/2008 | Brown et al. |
| 2008/0145923 A1 | 6/2008 | Hahn et al. |
| 2008/0153091 A1 | 6/2008 | Brown et al. |
| 2008/0160525 A1 | 7/2008 | Brown et al. |
| 2008/0161420 A1 | 7/2008 | Shuber |
| 2008/0166793 A1 | 7/2008 | Beer et al. |
| 2008/0169184 A1 | 7/2008 | Brown et al. |
| 2008/0169195 A1 | 7/2008 | Jones et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171380 A1 | 7/2008 | Brown et al. |
| 2008/0171382 A1 | 7/2008 | Brown et al. |
| 2008/0213766 A1 | 9/2008 | Brown et al. |
| 2008/0214407 A1 | 9/2008 | Remacle et al. |
| 2008/0262384 A1 | 10/2008 | Wiederkehr et al. |
| 2008/0268436 A1 | 10/2008 | Duan et al. |
| 2008/0274455 A1 | 11/2008 | Puskas et al. |
| 2008/0280331 A1 | 11/2008 | Davies et al. |
| 2008/0280865 A1 | 11/2008 | Tobita |
| 2008/0280955 A1 | 11/2008 | McCamish |
| 2008/0314761 A1 | 12/2008 | Herminghaus et al. |

(56) References Cited

U.S. PATENT DOCUMENTS

| | | |
|---|---|---|
| 2009/0012187 A1 | 1/2009 | Chu et al. |
| 2009/0026082 A1 | 1/2009 | Rothberg et al. |
| 2009/0029867 A1 | 1/2009 | Reed et al. |
| 2009/0035770 A1 | 2/2009 | Mathies et al. |
| 2009/0035838 A1 | 2/2009 | Quake et al. |
| 2009/0061428 A1 | 3/2009 | McBride et al. |
| 2009/0068170 A1 | 3/2009 | Weitz et al. |
| 2009/0069194 A1 | 3/2009 | Ramakrishnan |
| 2009/0098044 A1 | 4/2009 | Kong et al. |
| 2009/0114043 A1 | 5/2009 | Cox |
| 2009/0131543 A1 | 5/2009 | Weitz et al. |
| 2009/0162929 A1 | 6/2009 | Ikeda |
| 2009/0176271 A1 | 7/2009 | Durack et al. |
| 2009/0203063 A1 | 8/2009 | Wheeler et al. |
| 2009/0217742 A1 | 9/2009 | Chiu et al. |
| 2009/0220434 A1 | 9/2009 | Sharma |
| 2009/0235990 A1 | 9/2009 | Beer |
| 2009/0239308 A1 | 9/2009 | Dube et al. |
| 2009/0291435 A1 | 11/2009 | Unger et al. |
| 2009/0311713 A1 | 12/2009 | Pollack et al. |
| 2009/0325184 A1 | 12/2009 | Woudenberg et al. |
| 2009/0325234 A1 | 12/2009 | Gregg et al. |
| 2009/0325236 A1 | 12/2009 | Griffiths et al. |
| 2010/0009360 A1 | 1/2010 | Rosell Costa et al. |
| 2010/0020565 A1 | 1/2010 | Seward |
| 2010/0022414 A1 | 1/2010 | Link et al. |
| 2010/0041046 A1 | 2/2010 | Chiu et al. |
| 2010/0047808 A1 | 2/2010 | Reed et al. |
| 2010/0069250 A1 | 3/2010 | White, III et al. |
| 2010/0069263 A1 | 3/2010 | Shendure et al. |
| 2010/0092973 A1 | 4/2010 | Davies et al. |
| 2010/0137163 A1 | 6/2010 | Link et al. |
| 2010/0173394 A1 | 7/2010 | Colston, Jr. et al. |
| 2010/0248385 A1 | 9/2010 | Tan et al. |
| 2010/0261229 A1 | 10/2010 | Lau et al. |
| 2010/0304446 A1 | 12/2010 | Davies et al. |
| 2010/0304978 A1 | 12/2010 | Deng et al. |
| 2011/0000560 A1 | 1/2011 | Miller et al. |
| 2011/0027394 A1 | 2/2011 | McClements et al. |
| 2011/0053798 A1 | 3/2011 | Hindson et al. |
| 2011/0070589 A1 | 3/2011 | Belgrader et al. |
| 2011/0086780 A1 | 4/2011 | Colston, Jr. et al. |
| 2011/0092373 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0118151 A1 | 5/2011 | Eshoo et al. |
| 2011/0160078 A1 | 6/2011 | Fodor et al. |
| 2011/0177563 A1 | 7/2011 | Hahn et al. |
| 2011/0183330 A1 | 7/2011 | Lo et al. |
| 2011/0212516 A1 | 9/2011 | Ness et al. |
| 2011/0217712 A1 | 9/2011 | Hiddessen et al. |
| 2011/0218123 A1 | 9/2011 | Weitz et al. |
| 2011/0244455 A1 | 10/2011 | Larson et al. |
| 2011/0250597 A1 | 10/2011 | Larson et al. |
| 2011/0311978 A1 | 12/2011 | Makarewicz, Jr. et al. |
| 2012/0021423 A1 | 1/2012 | Colston, Jr. et al. |
| 2012/0028311 A1 | 2/2012 | Colston, Jr. et al. |
| 2012/0122714 A1 | 5/2012 | Samuels et al. |
| 2012/0152369 A1 | 6/2012 | Hiddessen et al. |
| 2012/0171683 A1 | 7/2012 | Ness et al. |
| 2012/0190032 A1 | 7/2012 | Ness et al. |
| 2012/0190033 A1 | 7/2012 | Ness et al. |
| 2012/0194805 A1 | 8/2012 | Ness et al. |
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0264646 A1 | 10/2012 | Link et al. |
| 2012/0302448 A1 | 11/2012 | Hutchison et al. |
| 2012/0309002 A1 | 12/2012 | Link |
| 2012/0329664 A1 | 12/2012 | Saxonov et al. |
| 2013/0017551 A1 | 1/2013 | Dube |
| 2013/0040841 A1 | 2/2013 | Saxonov et al. |
| 2013/0045875 A1 | 2/2013 | Saxonov et al. |
| 2013/0059754 A1 | 3/2013 | Tzonev |
| 2013/0064776 A1 | 3/2013 | El Harrak et al. |
| 2013/0084572 A1 | 4/2013 | Hindson et al. |
| 2013/0099018 A1 | 4/2013 | Miller et al. |
| 2013/0109575 A1 | 5/2013 | Kleinschmidt et al. |

FOREIGN PATENT DOCUMENTS

| | | |
|---|---|---|
| GB | 1 503 163 | 3/1978 |
| GB | 2 097 692 | 11/1982 |
| JP | 0295433 | 4/1990 |
| WO | 82/02562 | 8/1982 |
| WO | 84/02000 | 5/1984 |
| WO | 92/01812 | 2/1992 |
| WO | 94/05414 | 3/1994 |
| WO | 96/12194 | 4/1996 |
| WO | 98/00231 | 1/1998 |
| WO | 98/16313 | 4/1998 |
| WO | 98/44151 | 10/1998 |
| WO | 98/44152 | 10/1998 |
| WO | 98/47003 | 10/1998 |
| WO | 01/07159 | 2/2001 |
| WO | 01/12327 | 2/2001 |
| WO | 02/23163 | 3/2002 |
| WO | 02/060584 | 8/2002 |
| WO | 02/068104 | 9/2002 |
| WO | 02/081490 | 10/2002 |
| WO | 02/081729 | 10/2002 |
| WO | 03/016558 | 2/2003 |
| WO | 03/042410 | 5/2003 |
| WO | 03/072258 | 9/2003 |
| WO | 2004/040001 | 5/2004 |
| WO | 2005/007812 | 1/2005 |
| WO | 2005/010145 | 2/2005 |
| WO | 2005/021151 | 3/2005 |
| WO | 2005/023091 | 3/2005 |
| WO | 2005/055807 | 6/2005 |
| WO | 2005/073410 | 8/2005 |
| WO | 2005/075683 | 8/2005 |
| WO | 2006/023719 | 3/2006 |
| WO | 2006/027757 | 3/2006 |
| WO | 2006/038035 | 4/2006 |
| WO | 2006/086777 | 8/2006 |
| WO | 2006/095981 | 9/2006 |
| WO | 2007/091228 | 8/2007 |
| WO | 2007/091230 | 8/2007 |
| WO | 2007/092473 | 8/2007 |
| WO | 2007/133710 | 11/2007 |
| WO | 2008/021123 | 2/2008 |
| WO | 2008/024114 | 2/2008 |
| WO | 2008/063227 | 5/2008 |
| WO | 2008/070074 | 6/2008 |
| WO | 2008/070862 | 6/2008 |
| WO | 2008/109878 | 9/2008 |
| WO | 2008/112177 | 9/2008 |
| WO | WO2008109176 | * 9/2008 |
| WO | 2009/002920 | 12/2008 |
| WO | 2009/015863 | 2/2009 |
| WO | 2009/049889 | 4/2009 |
| WO | 2009/085246 | 7/2009 |
| WO | 2010/001419 | 1/2010 |
| WO | 2010/018465 | 2/2010 |
| WO | 2011/034621 | 3/2011 |
| WO | 2011/079176 | 6/2011 |

OTHER PUBLICATIONS

Young, Lee W., Authorized officer, International Searching Authority, Written Opinion of the International Searching Authority, PCT Application No. PCT/US 201046519; mail date: Oct. 15, 2010.

J. Smid-Korbar et al., "Efficiency and usability of silicone surfactants in emulsions," International Journal of Cosmetic Science 12, pp. 135-139, (1990), presented at the 15th IFSCC International Congress, Sep. 26-29, 1988, London.

A. Chittofrati et al., "Perfluoropolyether microemulsions," Progress in Colloid & Polymer Science 79, pp. 218-225, (1989).

Steven A. Snow, "Synthesis and Characterization of Zwitterionic Silicone Sulfobetaine Surfactants," Langmuir, vol. 6, No. 2, American Chemical Society, pp. 385-391, (1990).

Polydimethylsiloxane, 5 pgs., published in FNP 52 (1992).

(56) References Cited

OTHER PUBLICATIONS

Russell Higuchi et al., "Kinetic PCR Analysis: Real-time Monitoring of DNA Amplification Reactions," Bio/Technology vol. II, pp. 1026-1030, Sep. 11, 1993.
D. A. Newman et al., "Phase Behavior of Fluoroether-Functional Amphiphiles in Supercritical Carbon Dioxide," The Journal of Supercritical Fluids, vol. 6, No. 4, pp. 205-210, (1993).
Y. Sela et al., "Newly designed polysiloxane-graft-poly (oxyethylene) copolymeric surfactants: preparation, surface activity and emulsification properties," Colloid & Polymer Science 272, pp. 684-691, (1994).
M. Gasperlin et al., "The structure elucidation of semisolid w/o emulsion systems containing silicone surfactant," International Journal of Pharmaceutics 107, pp. 51-56, (1994).
Mieczyslaw A. Piatyszek et al., "Detection of telomerase activity in human cells and tumors by a telomeric repeat amplification protocol (TRAP)," Methods in Cell Science 17, pp. 1-15, (1995).
Anthony P. Shuber et al., "A Simplified Procedure for Developing Multiplex PCRs," Genome Research, published by Cold Spring Harbor Laboratory Press, pp. 488-493, (1995).
A. V. Yazdi et al., "Highly Carbon Dioxide Soluble Surfactants, Dispersants and Chelating Agents," Fluid Phase Equilibria, vol. 117, pp. 297-303, (1996).
Ariel A. Avilion et al., "Human Telomerase RNA and Telomerase Activity in Immortal Cell Lines and Tumor Tissues," Cancer Research 56, pp. 645-650, Feb. 1, 1996.
Shuming Nie et al., "Optical Detection of Single Molecules," Annu. Rev. Biophys. BiomoL Struct. vol. 26, pp. 567-596, (1997).
Edith J. Singley et al., "Phase behavior and emulsion formation of novel fluoroether amphiphiles in carbon dioxide," Fluid Phase Equilibria 128, pp. 199-219, (1997).
Olga Kalinina et al., "Nanoliter scale PCR with TaqMan Detection," Nucleic Acids Research, vol. 25, No. 10 pp. 1999-2004, (1997).
Zhen Guo et al., "Enhanced discrimination of single nucleotide polymorphisms by artificial mismatch hybridization," Nature Biotechnology vol. 15, pp. 331-335, Apr. 1997.
E. G. Ghenciu et al., "Affinity Extraction into Carbon Dioxide. 1. Extraction of Avidin Using a Biotin-Functional Fluoroether Surfactant," Ind. Eng. Chem. Res. vol. 36, No. 12, pp. 5366-5370, Dec. 1, 1997.
Paschalis Alexandridis, Structural Polymorphism of Poly(ethylene oxide)-Poly(propylene oxide) Block Copolymers in Nonaqueous Polar Solvents, Macromolecules, vol. 31, No. 20, pp. 6935-6942, Sep. 12, 1998.
Sandro R. P. Da Rocha et al., "Effect of Surfactants on the Interfacial Tension and Emulsion Formation between Water and Carbon Dioxide," Langmuir, vol. 15, No. 2, pp. 419-428, (1999), published on web Dec. 29, 1998.
Bert Vogelstein et al., "Digital PCR," Proc. Natl. Acad. Sci. USA, vol. 96, pp. 9236-9241, Aug. 1999.
Anthony J. O'Lenick, Jr., "Silicone Emulsions and Surfactants," Journal of Surfactants and Detergents, vol. 3, No. 3, Jul. 2000.
N. Garti et al., "Water Solubilization in Nonionic Microemulsions Stabilized by Grafted Siliconic Emulsifiers," Journal of Colloid and Interface Science vol. 233, pp. 286-294, (2001).
Shinji Katsura et al., "Indirect micromanipulation of single molecules in water-in-oil emulsion," Electrophoresis, vol. 22, pp. 289-293, (2001).
Hironobu Kunieda et al., "Effect of Hydrophilic- and Hydrophobic-Chain Lengths on the Phase Behavior of A-B-type Silicone Surfactants in Water," J. Phys. Chem. B, vol. 105, No. 23, pp. 5419-5426, (2001).
Hidenori Nagai et al., "Development of a Microchamber Array for Picoliter PCR," Analytical Chemistry, vol. 73, No. 5, pp. 1043-1047, Mar. 1, 2001.
Christopher B. Price, "Regular Review Point of Care Testing," BMJ, vol. 322, May 26, 2001.
3M Specialty Materials, "3M Fluorinert Electronic Liquid FC-3283," product information guide, issued Aug. 2001.
Ivonne Schneegaß et al., "Miniaturized flow-through PCR with different template types in a silicon chip thermocycler," Lab on a Chip, vol. 1, pp. 42-49, (2001).
Randla M. Hill, "Silicone surfactants—new developments," Current Opinion in Colloid & Interface Science 7, pp. 255-261, (2002).
Richard M. Cawthon, "Telomere measurement by quantitative PCR," Nucleic Acids Research, vol. 30, No. 10, pp. 1-6, (2002).
Anfeng Wang et al., "Direct Force Measurement of Silicone- and Hydrocarbon-Based ABA Triblock Surfactants in Alcoholic Media by Atomic Force Mircroscopy," Journal of Colloid and Interface Science 256, pp. 331-340 (2002).
Shelley L. Anna et al., "Formation of dispersions using "flow focusing" in microchannels," Applied Physics Letters, vol. 82, No. 3, Jan. 20, 2003.
Goldschmidt GmbH, "Abil® EM 90 Emulsifier for the formulation of cosmetic W/O creams and lotions," degussa. creating essentials brochure, pp. 1-7, May 2003.
Purnendu K. Dasgupta et al., "Light emitting diode-based detectors Absorbance, fluorescence and spectroelectrochemical measurements in a planar flow-through cell," Analytica Chimica Acta 500, pp. 337-364, (2003).
R. G. Rutledge et al., "Mathematics of quantitative kinetic PCR and the application of standard curves," Nucleic Acids Research, vol. 31, No. 16, pp. 1-6, (2003).
Chunming Ding et al., "Direct molecular haplotyping of long-range genomic DNA with M1-PCR," PNAS, vol. 100, No. 13, pp. 7449-7453, Jun. 24, 2003.
Devin Dressman et al., "Transforming single DNA molecules into fluorescent magnetic particles for detection and enumeration of genetic variations," PNAS, vol. 100, No. 15, Jul. 22, 2003.
Ulf Landegren et al., "Padlock and proximity probes for in situ and array-based analyses: tools for the post-genomic era," Comp. Funct. Genom, vol. 4, pp. 525-530, (2003).
Gudrun Pohl et al., "Principle and applications of digital PCR" review, www.future-drugs.com, Expert Rev. Mol. Diagn. 4(1), pp. 41-47, (2004).
Groff M. Schroeder et al., "Introduction to Flow Cytometry" version 5.1, 182 pgs. (2004).
Stéphane Swillens et al., "Instant evaluation of the absolute initial number of cDNA copies from a single real-time PCR curve," Nucleic Acids Research, vol. 32, No. 6, pp. 1-6, (2004).
Mats Gullberg et al., "Cytokine detection by antibody-based proximity ligation," PNAS, vol. 101, No. 22, pp. 8420-8424, Jun. 1, 2004.
Tianhao Zhang et al., "Behavioral Modeling and Performance Evaluation of Microelectrofluidics-Based PCR Systems Using SystemC," IEEE Transactions on Computer-Aided Design of Integrated Circuits and Systems, vol. 23, No. 6, pp. 843-858, Jun. 2004.
R. G. Rutledge, "Sigmoidal curve-fitting redefines quantitative real-time PCR with the prospective of developing automated high-throughput applications," Nucleic Acids Research. vol. 32, No. 22, pp. 1-8, (2004).
L. Spencer Roach et al., "Controlling Nonspecific Protein Absorption in a Plug-Based Microfluidic System by Controlling Interfacial Chemistry Using Fluorous-Phase Surfactants," Analytical Chemistry vol. 77, No. 3, pp. 785-796, Feb. 1, 2005.
Kevin D. Dorfman et al., "Contamination-Free Continuous Flow Microfluidic Polymerase Chain Reaction for Quantitative and Clinical Applications," Analytical Chemistry vol. 77, No. 11, pp. 3700-3704, Jun. 1, 2005.
James G. Wetmur et al., "Molecular haplotyping by linking emulsion PCR: analysis of paraoxonase 1 haplotypes and phenotypes," Nucleic Acids Research, vol. 33, No. 8, pp. 2615-2619, (2005).
Piotr Garstecki et al., "Mechanism for Flow-Rate Controlled Breakup in Confined Geometries: A Route to Monodisperse Emulsions," Physical Review Letters, 164501, pp. 164501-1-164501-4, Apr. 29, 2005.
Anna Musyanovych et al., "Miniemulsion Droplets as Single Molecule Nanoreactors for Polymerase Chain Reaction," Biomacromolecules, vol. 6, No. 4, pp. 1824-1828, (2005).
Max Chabert et al., "Droplet fusion by alternating current (AC) field electrocoalescence in microchannels," Electrophoresis, vol. 26, pp. 3706-3715, (2005).

(56) References Cited

OTHER PUBLICATIONS

Takaaki Kojima et al., "PCR amplification from single DNA molecules on magnetic beads in emulsion: application for high-throughput screening of transcription factor targets," Nucleic Acids Research, vol. 33, No. 17, pp. 1-9, (2005).

Marcel Margulies et al., "Genome sequencing in microfabricated high-density picolitre reactors," Nature, vol. 437, 51 pgs., Sep. 15, 2005.

Kristofer J. Thurecht et al., "Investigation of spontaneous microemulsion formation in supercritical carbon dioxide using high-pressure NMR," Journal of Supercritical Fluids, vol. 38, pp. 111-118, (2006).

Toshko Zhelev et al., "Heat Integration in Micro-Fluidic Devices," 16th European Symposium on Computer Aided Process Engineering and 9th International Symposium on Process Systems Engineering, pp. 1863-1868 published by Elsevier B.V. (2006).

Piotr Garstecki et al., "Formation of droplets and bubbles in a microfluidic T-junction—scaling and mechanism of break-up," Lab on a Chip, vol. 6, pp. 437-446, (2006).

Darren R. Link et al., "Electric Control of Droplets in Microfluidic Devices," Angewandte Chemie Int. Ed., vol. 45, pp. 2556-2560, (2006).

Peter Fielden et al., "Micro-Droplet Technology for High Throughout Systems and Methods," 1 pg., Mar. 8, 2006.

David Emerson et al., "Microfluidic Modelling Activities at C3M," Centre for Microfluidics & Microsystems Modelling, Daresbury Laboratory, pp. 1-26, May 15, 2006.

Richard Williams et al., "Amplification of complex gene libraries by emulsion PCR," Nature Methods, vol. 3, No. 7, pp. 545-550, Jul. 2006.

John H. Leamon et al., "Overview: methods and applications for droplet compartmentalization of biology," Nature Methods, vol. 3, No. 7, pp. 541-543, Jul. 2006.

Andrew D. Griffiths et al., "Miniaturising the laboratory in emulsion droplets," TRENDS in Biotechnology, vol. 24, No. 9, pp. 395-402, Jul. 14, 2006.

Jian-Bing Fan et al., "Highly parallel genomic assays," Nature Reviews/Genetics, vol. 7, pp. 632-644, Aug. 2006.

Jonas Jarvius et al., "Digital quantification using amplified single-molecule detection," Nature Methods, vol. 3, No. 9, pp. 15 pgs, Sep. 2006.

Kan Liu et al., "Droplet-based synthetic method using microflow focusing and droplet fusion," Microfluid Nanfluid, vol. 3, pp. 239-243, (2007), published online Sep. 22, 2006.

Dimitris Glotsos et al., "Robust Estimation of Bioaffinity Assay Fluorescence Signals," IEEE Transactions on Information Technology in Biomedicine, vol. 10, No. 4, pp. 733-739, Oct. 2006.

Kristofer J. Thurecht et al., "Kinetics of Enzymatic Ring-Opening Polymerization of □-Caprolactone in Supercritical Carbon Dioxide," Macromolecules, vol. 39, pp. 7967-7972, (2006).

Machiko Hori et al., "Uniform amplification of multiple DNAs by emulsion PCR," Biochemical and Biophysical Research Communications, vol. 352, pp. 323-328, (2007).

Frank Diehl et al., "Digital quantification of mutant DNA in cancer patients," Current Opinion in Oncology, vol. 19, pp. 36-42, (2007).

Delai L. Chen et al., "Using Three-Phase Flow of Immiscible Liquids to Prevent Coalescence of Droplets in Microfluidic Channels: Criteria to Identify the Third Liquid and Validation with Protein Crystallization," Langmuir, vol. 23, No. 4, pp. 2255-2260, (2007).

S. Mohr et al., "Numerical and experimental study of a droplet-based PCR chip," Microfluid Nanofluid, vol. 3, pp. 611-621, (2007).

Sigrun M. Gustafsdottir et al., "In vitro analysis of DNA-protein interactions by proximity ligation," PNAS, vol. 104, No. 9, pp. 3067-3072, Feb. 27, 2007.

Daniel J. Diekema et al., "Look before You Leap: Active Surveillance for Multidrug-Resistant Organisms," Healthcare Epidemiology • CID 2007:44, pp. 1101-1107 (Apr. 15), electronically published Mar. 2, 2007.

Charles N. Baroud et al., "Thermocapillary valve for droplet production and sorting," Physical Review E 75, 046302, pp. 046302-1-046302-5, Apr. 5, 2007.

Qinyu Ge et al., "Emulsion PCR-based method to detect Y chromosome microdeletions," Analytical Biochemistry, vol. 367, pp. 173-178, May 10, 2007.

Chunsun Zhang et al., "Miniaturized PCR chips for nucleic acid amplification and analysis: latest advances and future trends," Nucleic Acids Research, vol. 35, No. 13, pp. 4223-4237, Jun. 18, 2007.

Y. M. Dennis Lo et al., "Digital PCR for the molecular detection of fetal chromosomal aneuploidy," PNAS, vol. 104, No. 32, pp. 13116-13121, Aug. 7, 2007.

Dayong Jin et al., "Practical Time-Gated Luminescence Flow Cytometry. II: Experimental Evaluation Using UV LED Excitation," Cytometry Part A • 71A, pp. 797-808, Aug. 24, 2007.

Helen R. Hobbs et al., "Homogeneous Biocatalysis in both Fluorous Biphasic and Supercritical Carbon Dioxide Systems," Angewandte Chemie, vol. 119, pp. 8006-8009, Sep. 6, 2007.

Nathan Blow, "PCR's next frontier," Nature Methods, vol. 4, No. 10, pp. 869-875, Oct. 2007.

Nicole Pamme, "continuous flow separations in microfluidic devices," Lab on a Chip, vol. 7, pp. 1644-1659, Nov. 2, 2007.

N. Reginald Beer et al., "On-Chip, Real-Time, Single-Coy Polymerase Chain Reaction in Picoliter Droplets," Analytical Chemistry, vol. 79, No. 22, pp. 8471-8475, Nov. 15, 2007.

Yuejun Zhao et al., "Microparticle Concentration and Separation by Traveling-Wave Dielectrophoresis (twDEP) for Digital Microfluidics," Journal of Microelectromechanical Systems, vol., 16, No. 6, pp. 1472-1481, Dec. 2007.

Sigma-Aldrich, "Synthesis of Mesoporous Materials," Material Matters, 3.1, 17, (2008).

Nick J. Carroll et al., "Droplet-Based Microfluidics for Emulsion and Solvent Evaporation Synthesis of Monodisperse Mesoporous Silica Microspheres," Langmuir, vol. 24, No. 3, pp. 658-661, Jan. 3, 2008.

Shia-Yen Teh et al., "Droplet microfluidics," Lab on a Chip, vol. 8, pp. 198-220, Jan. 11, 2008.

Chloroform (Phenomenex), Solvent Miscibility Table, Internet Archive WayBackMachine, 3 pgs., Feb. 1, 2008.

N. Reginald Beer et al., "On-Chip Single-Copy Real-Time Reverse-Transcription PCR in Isolated Picoliter Droplets," Analytical Chemistry, vol. 80, No. 6, pp. 1854-1858, Mar. 15, 2008.

Palani Kumaresan et al., "High-Throughput Single Copy DNA Amplification and Cell Analysis in Engineered Nanoliter Droplets," Analytical Chemistry, 17 pgs., Apr. 15, 2008.

Somil C. Mehta et a., "Mechanism of Stabilization of Silicone Oil—Water Emulsions Using Hybrid Siloxane Polymers," Langmuir, vol. 24, No. 9, pp. 4558-4563, Mar. 26, 2008.

Rhutesh K. Shah et al., "Polymers fit for function Making emulsions drop by drop," Materials Today, vol. 11, No. 4, pp. 18-27, Apr. 2008.

Mohamed Abdelgawad et al., "All-terrain droplet actuation," Lab on a Chip, vol. 8, pp. 672-677, Apr. 2, 2008.

Lung-Hsin Hung et al., "Rapid microfabrication of solvent-resistant biocompatible microfluidic devices," Lab on a Chip, vol. 8, pp. 983-987, Apr. 8, 2008.

Jenifer Clausell-Tormos et al., "Droplet-Based Microfluidic Platforms for the Encapsulation and Screening of Mammalian Cells and Multicellular Organisms," Chemistry & Biology, vol. 15, pp. 427-437, May 2008.

Vivienne N. Luk et al., "Pluronic Additives: A Solution to Sticky Problems in Digital Microfluidics," Langmuir, vol. 24, No. 12, pp. 6382-6289, May 16, 2008.

Yen-Heng Lin et al., "Droplet Formation Utilizing Controllable Moving-Wall Structures for Double-Emulsion Applications," Journal of Microelectromechanical Systems, vol. 17, No. 3, pp. 573-581, Jun. 2008.

Simant Dube et al., "Mathematical Analysis of Copy Number Variation in a DNA Sample Using Digital PCR on a Nanofluidic Device," PLoS ONE, vol. 3, Issue 8, pp. 1-9, Aug. 6, 2008.

Jian Qin et al., "Studying copy number variations using a nanofluidic platform," Nucleic Acids Research, vol. 36, No. 18, pp. 1-8, Aug. 18, 2008.

(56) References Cited

OTHER PUBLICATIONS

C. Holtze et al., "Biocompatible surfactants for water-in-fluorocarbon emulsions," Lab on a Chip, vol. 8, pp. 1632-1639, Sep. 2, 2008.
Margaret Macris Kiss et al., "High-Throughput Quantitative Polymerase Chain Reaction in Picoliter Droplets," Analytical Chemistry, 8 pgs., downloaded Nov. 17, 2008.
Jay Shendure et al., "Next-generation DNA sequencing," Nature Biotechnology, vol. 26, No. 10, pp. 1135-1145, Oct. 2008.
Bernhard G. Zimmermann et al., "Digital PCR: a powerful new tool for noninvasive prenatal diagnosis?," Prenatal Diagnosis, vol. 28 pp. 1087-1093, Nov. 10, 2008.
Avishay Bransky et al., "A microfluidic droplet generator based on a piezoelectric actuator," Lab on a Chip, vol. 9, pp. 516-520, Nov. 20, 2008.
David A. Weitz, "Novel Surfactants for Stabilizing Emulsions of Water or Hydrocarbon Oil-Based Droplets in a Fluorocarbon Oil Continuous Phase," Harvard Office of Technology Development: Available Technologies, pp. 1-3, downloaded Nov. 28, 2008.
Neil Reginald Beer et al., "Monodisperse droplet generation and rapid trapping for single molecule detection and reaction kinetics measurement," Lab on a Chip, vol. 9, pp. 841-844, Dec. 5, 2008.
Richard M. Cawthon, "Telomere length measurement by a novel monochrome multiplex quantitative PCR method," Nucleic Acids Research, vol. 37, No. 3, pp. 1-7, (2009).
Anthony J. O'Lenick, Jr., "Silicone Emulsions and Surfactants—A Review," Silicone Spectator, Silitech LLC, May 2009 (original published May 2000).
Adam R. Abate et al., "Functionalized glass coating for PDMS microfluidic devices," Lab on a Chip Technology: Fabrication and Microfluidics, 11 pgs., (2009).
Chia-Hung Chen et al., "Janus Particles Templated from Double Emulsion Droplets Generated Using Microfluidics," Langmuir, vol. 29, No. 8, pp. 4320-4323, Mar. 18, 2009.
Luis M. Fidalgo et al., "Coupling Microdroplet Microreactors with Mass Spectrometry: Reading the Contents of Single Droplets Online," Angewandte Chemie, vol. 48, pp. 3665-3668, Apr. 7, 2009.
Linas Mazutis et al., "A fast and efficient microfluidic system for highly selective one-to-one droplet fusion," Lab on a Chip, vol. 9, pp. 2665-2672, Jun. 12, 2009.
Linas Mazutis et al., "Droplet-Based Microfluidic Systems for High-Throughput Single DNA Molecule Isothermal Amplification and Analysis," Analytical Chemistry, vol. 81, No. 12, pp. 4813-4821, Jun. 15, 2009.
Frank McCaughan et al., "Single-molecule genomics," Journal of Pathology, vol. 220, pp. 297-306, Nov. 19, 2009.
Suzanne Weaver et al., "Taking qPCR to a higher level: Analysis of CNV reveals the power of high throughput qPCR to enhance quantitative resolution," Methods, vol. 50, pp. 271-276, Jan. 15, 2010.
Amelia L. Markey et al., "High-throughput droplet PCR," Methods, vol. 50, pp. 277-281, Feb. 2, 2010.
Yoon Sung Nam et al., "Nanosized Emulsions Stabilized by Semi-solid Polymer Interphase," Langmuir, ACS Publications, Jul. 23, 2010.
Tatjana Schütze et al., "A streamlined protocol for emulsion polymerase chain reaction and subsequent purification," Analytical Biochemistry, vol. 410, pp. 155-157, Nov. 25, 2010.
Somanath Bhat et al., "Effect of sustained elevated temperature prior to amplification on template copy number estimation using digital polymerase chain reaction," Analyst, vol. 136, pp. 724-732, (2011).
James G. Wetmur, et al., "Linking Emulsion PCR Haplotype Analysis," PCR Protocols, Methods in Molecular Biology, vol. 687, pp. 165-175, (2011).
Paul Vulto et al., "Phaseguides: a paradigm shift in microfluidic priming and emptying," Lab on a Chip, vol. 11, No. 9, pp. 1561-1700, May 7, 2011.
Thinxxs Microtechnology AG, "Emerald Biosystems: Protein Crystallization," 1 pg., downloaded Mar. 8, 2011.
Qun Zhong et al., "Multiplex digital PCR: breaking the one target per color barrier of quantitative PCR," Lab on a Chip, vol. 11, pp. 2167-2174, (2011).
Jiaqi Huang et al., "Rapid Screening of Complex DNA Samples by Single-Molecule Amplification and Sequencing," PLoS ONE, vol. 6, Issue 5, pp. 1-4, May 2011.
Burcu Kekevi et al., Synthesis and Characterization of Silicone-Based Surfactants as Anti-Foaming Agents, J. Surfact Deterg (2012), vol. 15, pp. 73-81, published online Jul. 7, 2011.
Leonardo B. Pinheiro et al., "Evaluation of a Droplet Digital Polymerase Chain Reaction Format for DNA Copy Number Quantification," Analytical Chemistry, vol. 84, pp. 1003-1011, Nov. 28, 2011.
Nicole L. Solimini et al., "Recurrent Hemizygous Deletions in Cancers May Optimize Proliferative Potential," Science, vol. 337, pp. 104-109, Jul. 6, 2012.
Labsmith, "Microfluid Components" webpage, downloaded Jul. 11, 2012.
Labsmith, "CapTite™ Microfluidic Interconnects" webpage, downloaded Jul. 11, 2012.
Nathan A. Tanner et al., "Simultaneous multiple target detection in real-time loop-mediated isothermal amplification," BioTechniques, vol. 53, pp. 8-19, Aug. 2012.
A. Scherer, California Institute of Technology, "Polymerase Chain Reactors" PowerPoint presentation, 24 pgs., date unknown.
Eschenback Optik GmbH, Optics for Concentrated Photovoltaics (CPV), 1 pg., date unknown.
Charles N. Baroud et al., "An optical toolbox for total control of droplet microfluidics", Lab on a Chip, vol. 7, Jun. 8, 2007, pp. 1029-1033.
Hanyoup Kim et al., "Nanodroplet real-time PCR system with laser assisted heating", Optics Express, vol. 17, No. 1, Jan. 5, 2009, pp. 218-227.

\* cited by examiner

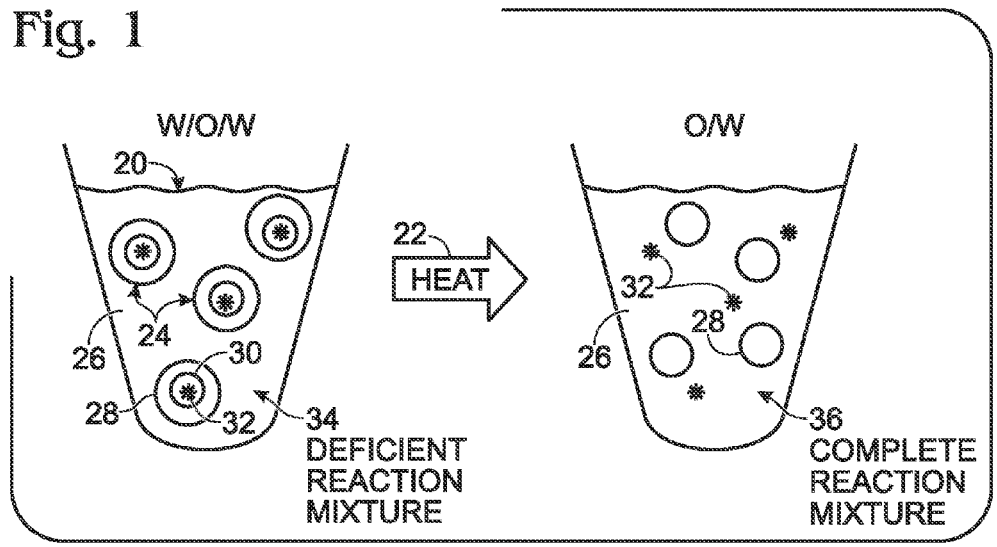
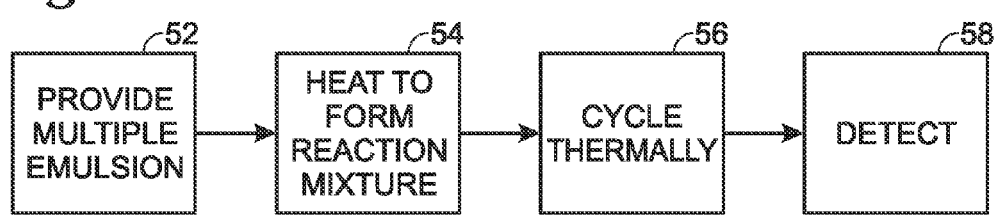
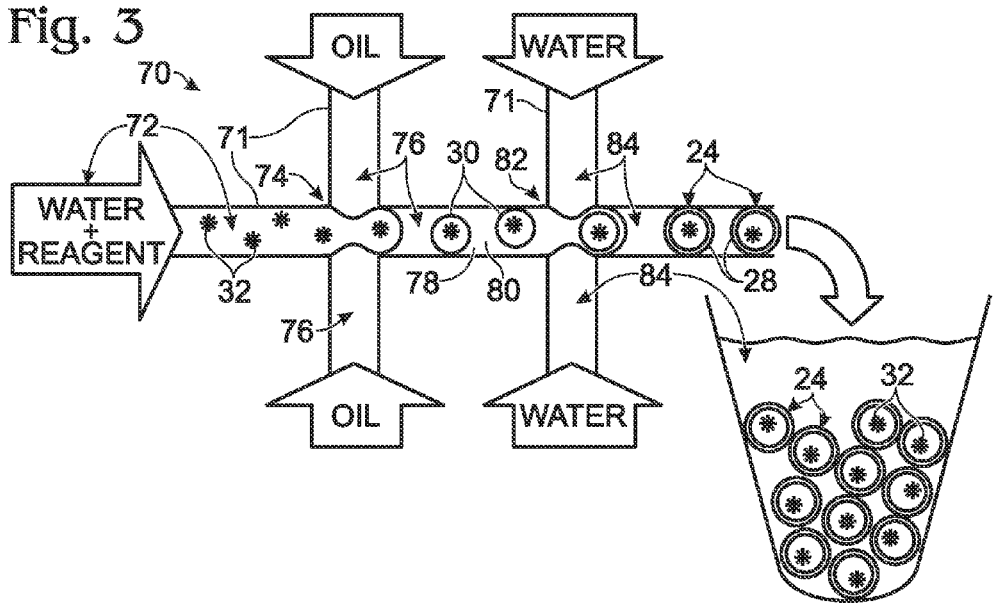

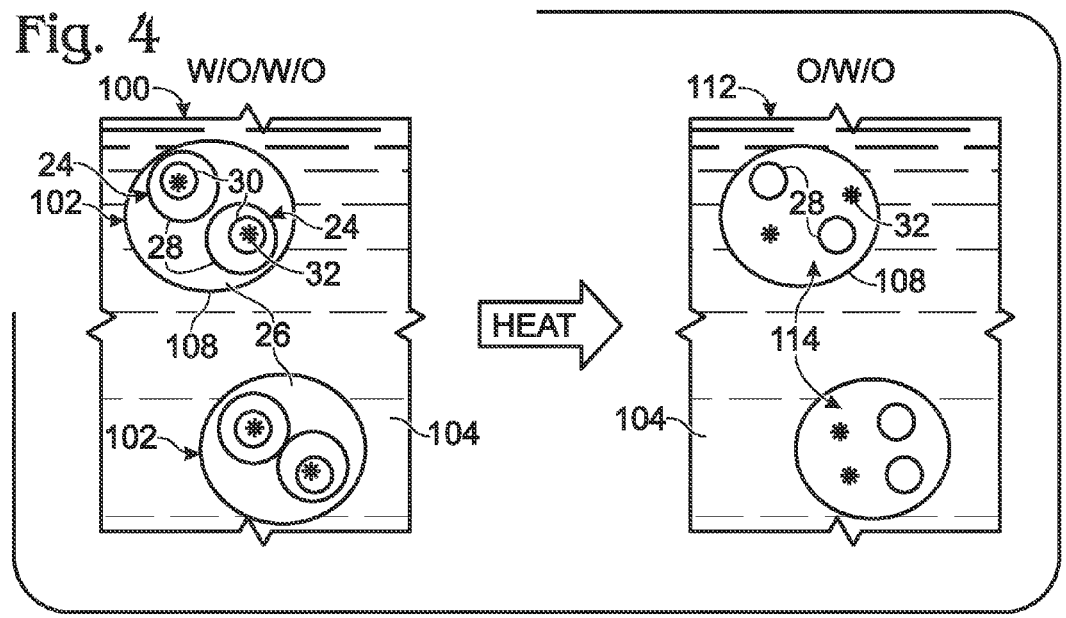
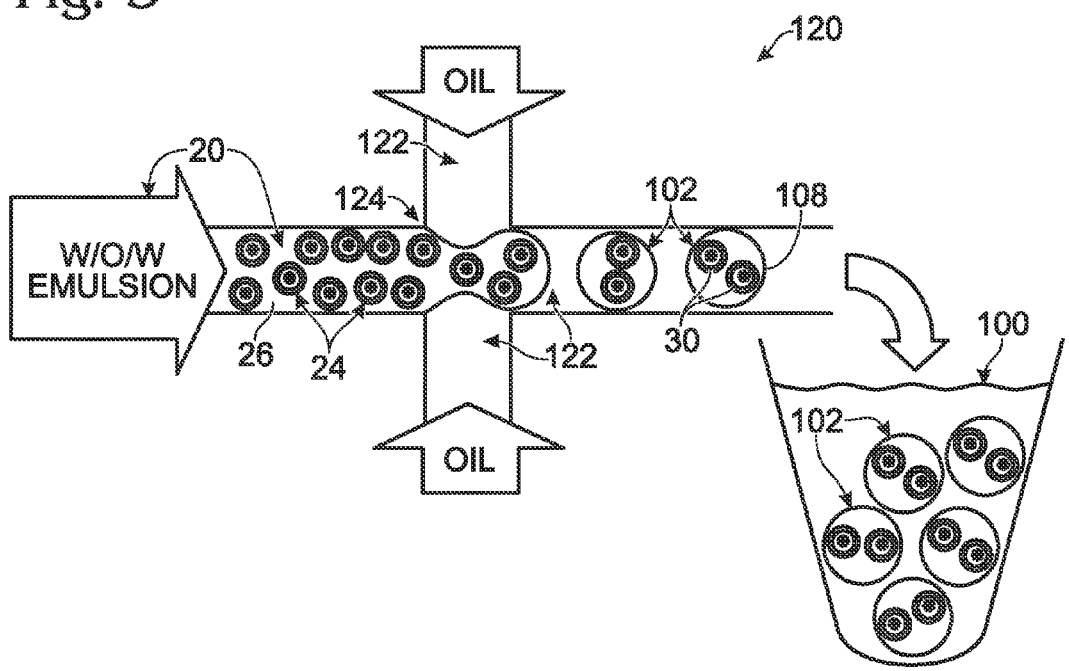

SYSTEM FOR HOT-START AMPLIFICATION VIA A MULTIPLE EMULSION

CROSS-REFERENCE TO PRIORITY APPLICATION

This application is based upon and claims the benefit under 35 U.S.C. §119(e) of U.S. Provisional Patent Application Ser. No. 61/309,837, filed Mar. 2, 2010, which is incorporated herein by reference in its entirety for all purposes.

CROSS-REFERENCES TO OTHER MATERIALS

This application incorporates by reference in their entireties for all purposes the following materials: U.S. Pat. No. 7,041,481, issued May 9, 2006; U.S. patent application Ser. No. 12/586,626, filed Sep. 23, 2009; U.S. patent application Ser. No. 12/862,542, filed Aug. 24, 2010; and U.S. patent application Ser. No. 12/976,827, filed Dec. 22, 2010.

INTRODUCTION

The polymerase chain reaction (PCR) utilizes repeated rounds of replication of a nucleic acid template, which may produce an exponential amplification of the template's copy number. PCR amplification relies on changes in the temperature of a reaction mixture to produce repeated cycles of template replication. Each replication cycle may be driven by a thermal cycle that involves (1) template denaturation at a higher temperature, (2) annealing of one or more primers to the denatured template at a lower temperature, and (3) extension of the annealed primers with a heat-stable DNA polymerase, such as Taq DNA polymerase, at a lower or intermediate temperature, to form complementary strands of the template.

Interfering side reactions can occur in a PCR mixture before the first thermal cycle is initiated, if an active reaction mixture is formed before heating. In particular, primer annealing may be inaccurate when the reaction mixture is formed at a lower temperature than the annealing temperature utilized for PCR amplification. In this case, the reaction mixture generally is heated to a denaturation temperature through a temperature range starting at or below room temperature. As a result, DNA polymerase is active and can extend primers that are annealed incorrectly, such as to form primer dimers and/or non-specific products. These undesired products can consume primers and deoxynucleotide triphosphates and can function as templates that compete with the desired amplification reaction. Accordingly, premature primer extension can reduce the efficiency and yield of the amplification reaction, complicate interpretation of results, and, in some cases, may cause failure to amplify the specified target.

Strategies have been developed to delay formation of a competent amplification mixture until the mixture has been heated above the annealing temperature, to effect a "hot-start." Generally, in these strategies, an essential PCR reagent is inactive and/or sequestered until the reaction has been heated sufficiently.

The PCR reagent, such as a heat-stable polymerase (e.g., Taq DNA polymerase), may be held in an inactive complex by an antibody or an aptamer until the polymerase is released from the complex by heating. However, locking the polymerase in an inactive complex can be expensive and inefficient.

In another approach, the polymerase may be kept separate from other components of the reaction mixture. For example, the polymerase may be sequestered from the bulk aqueous solution by a wax layer that melts above the annealing temperature to unite the polymerase with the other reaction components and form a complete reaction mixture. In another example, the polymerase may be disposed in a wax bead that melts to release the polymerase. However, reaction mixtures using a distinct phase to sequester the polymerase can be inefficient to assemble because the distinct phase may not amenable to standard fluid transfer techniques.

There remains a need for other approaches to perform hot-start amplification of nucleic acids.

SUMMARY

The present disclosure provides a system, including methods, apparatus, compositions, and kits, for making and using compound droplets of a multiple emulsion to supply an amplification reagent, such as a heat-stable DNA polymerase or DNA ligase, to an aqueous phase in which the compound droplets are disposed. The compound droplets may be induced to supply the amplification reagent by heating the multiple emulsion, to achieve hot-start amplification.

BRIEF DESCRIPTION OF THE DRAWINGS

FIG. 1 is a schematic flow diagram illustrating an exemplary multiple emulsion being heated to promote fusion of aqueous droplets with a continuous aqueous phase, to form a mixture competent for nucleic acid amplification, in accordance with aspects of present disclosure.

FIG. 2 is a flowchart presenting an exemplary method of sample analysis using a multiple emulsion to controllably combine a sequestered reagent with other amplification reagents, in accordance with aspects of the present disclosure.

FIG. 3 is a schematic view of an exemplary system for forming compound droplets for use in the multiple emulsions of FIGS. 1 and 2, in accordance with aspects of the present disclosure.

FIG. 4 is a schematic flow diagram illustrating an exemplary multiple emulsion being heated to promote fusion of inner aqueous droplets with outer aqueous droplets that enclose the inner aqueous droplets, to form a complete reaction mixture for nucleic acid amplification in each outer droplet, in accordance with aspects of the present disclosure.

FIG. 5 is a schematic view of an exemplary system for forming the multiple emulsion of FIG. 4, in accordance with aspects of the present disclosure.

DETAILED DESCRIPTION

The present disclosure provides a system, including methods, apparatus, compositions, and kits, for making and using compound droplets of a multiple emulsion to supply an amplification reagent, such as a heat-stable polymerase or ligase, to an aqueous phase in which the compound droplets are disposed. The compound droplets may be induced to supply the amplification reagent by heating the multiple emulsion, to achieve hot-start amplification. The aqueous phase may be an incomplete reaction mixture for amplification due to a lack of the amplification reagent carried by the compound droplets. The amplification reagent may be sequestered in the compound droplets until an elevated temperature is reached, such as at least an annealing temperature, which may promote droplet fusion with the aqueous phase. Accordingly, the reaction mixture may not become complete (and competent for primer extension and/or ligation) until a suitable annealing stringency is achieved, thereby reducing formation of primer dimers and non-specific products.

A method of nucleic acid amplification is provided. In the method, a multiple emulsion may be provided that includes compound droplets disposed in an aqueous phase, which may be a continuous phase or a dispersed phase. The compound droplets may include at least one amplification reagent, such as a DNA polymerase (e.g., a heat-stable DNA polymerase, such as Taq polymerase), a heat-stable ligase, one or more dNTPs, magnesium (e.g., $Mg^{2+}$), at least one primer for a nucleic acid target, or a combination thereof. Each compound droplet may include at least one aqueous droplet enclosed by an oil droplet, and the aqueous droplet may contain the at least one amplification reagent. In any event, the multiple emulsion may be heated such that the at least one amplification reagent is released to the aqueous phase to form a reaction mixture. The reaction mixture may be cycled thermally to promote amplification of a nucleic acid target.

Another method of nucleic acid amplification is provided. In the method, a multiple emulsion may be provided that includes compound droplets disposed in an aqueous phase. The aqueous phase may lack an effective amount of at least one PCR reagent that is contained by the compound droplets. The multiple emulsion may be heated such that the at least one PCR reagent is added to the aqueous phase from the compound droplets to form a reaction mixture capable of PCR amplification of a nucleic acid target, if present, in the reaction mixture. The reaction mixture may be cycled thermally to encourage PCR amplification of the nucleic acid target.

Yet another method of nucleic acid amplification is provided. In the method, a multiple emulsion may be provided that includes compound droplets disposed in an aqueous phase, with each compound droplet including an oil droplet enclosing at least one aqueous droplet. The aqueous droplet may contain a heat-stable polymerase. The multiple emulsion may be heated such that aqueous droplets of the compound droplets fuse with the aqueous phase to supply an effective amount of the heat-stable polymerase to the aqueous phase, to form a reaction mixture capable of PCR amplification of a nucleic acid target, if present, in the reaction mixture. The reaction mixture may be cycled thermally to encourage PCR amplification.

A composition for nucleic acid amplification is provided. The composition may a multiple emulsion including compound droplets disposed in an aqueous phase, with each compound droplet including an oil droplet enclosing at least one aqueous droplet. The aqueous droplet may contain at least one amplification reagent. Heating the multiple emulsion may cause aqueous droplets of the compound droplets to fuse with the aqueous phase to supply the at least one reagent to the aqueous phase. Heating may form a reaction mixture capable of amplification of a nucleic acid target, if present, in the reaction mixture.

A kit is provided for use in nucleic acid amplification. The kit may include a first composition including compound droplets containing an amplification reagent. The kit also may include at least one second composition that is aqueous and that includes another amplification reagent.

Further aspects of the present disclosure are presented in the following sections: (I) definitions, (II) exemplary fusion of a multiple emulsion, (III) exemplary method of sample analysis using a multiple emulsion, (IV) exemplary system for forming compound droplets, (V) exemplary fusion within compound droplets, (VI) exemplary system for forming compound droplets that fuse internally, and (VII) selected embodiments.

I. Definitions

Technical terms used in this disclosure have the meanings that are commonly recognized by those skilled in the art. However, the following terms may have additional meanings, as described below.

Emulsion—a composition comprising liquid droplets disposed in an immiscible liquid. The droplets are formed by at least one dispersed phase, and the immiscible liquid forms a continuous phase. The continuous phase can also or alternatively be termed a carrier and/or a carrier phase. The dispersed phase (or at least one of the dispersed phases of a multiple emulsion) is immiscible with the continuous phase, which means that the dispersed phase (i.e., the droplets) and the continuous phase (i.e., the immiscible liquid) do not mix to attain homogeneity. The droplets are isolated from one another by the continuous phase and encapsulated (i.e., enclosed/surrounded) by the continuous phase.

The droplets of an emulsion may have any uniform or non-uniform distribution in the continuous phase. If non-uniform, the concentration of the droplets may vary to provide one or more regions of higher droplet density and one or more regions of lower droplet density in the continuous phase. For example, droplets may sink or float in the continuous phase.

An emulsion may be monodisperse, that is, composed of droplets of uniform size, or may be polydisperse, that is, composed of droplets of various sizes. If monodisperse, the droplets of the emulsion may vary in size by a standard deviation of the volume (or diameter) that is less than about 50%, 20%, 10%, 5%, 2%, or 1% of the average droplet volume (or diameter). Droplets generated from an orifice may be monodisperse or polydisperse.

A multiple emulsion disclosed herein may be a heat-sensitive emulsion. A heat-sensitive emulsion is any emulsion that can be induced to fuse when heated, such as to a temperature of less than about 90° C. or 95° C. For example, a heat-sensitive emulsion may be configured to fuse substantially when heated to at least about 50° C., 60° C., 70° C., 80° C., or 90° C., among others.

An emulsion may have any suitable composition. The emulsion may be characterized by the predominant liquid compound or type of liquid compound in each phase. The predominant liquid compounds in the emulsion may be one or more aqueous phases and one or more nonaqueous phases. The nonaqueous phase may be referred to as an oil phase comprising at least one oil, which generally includes any liquid (or liquefiable) compound or mixture of liquid compounds that is immiscible with water. The oil may be synthetic or naturally occurring. The oil may or may not include carbon and/or silicon, and may or may not include hydrogen and/or fluorine. The oil may be lipophilic or lipophobic. In other words, the oil may be generally miscible or immiscible with organic solvents. Exemplary oils may include at least one silicone oil, mineral oil, fluorocarbon oil, vegetable oil, or a combination thereof, among others.

In exemplary embodiments, the oil is a fluorinated oil, such as a fluorocarbon oil, which may be a perfluorinated organic solvent. A fluorinated oil may be a base (primary) oil or an additive to a base oil, among others. Exemplary fluorinated oils that may be suitable are sold under the trade name FLUORINERT (3M), including, in particular, FLUORINERT Electronic Liquid FC-3283, FC-40, FC-43, and FC-70. Another example of an appropriate fluorinated oil is sold under the trade name NOVEC (3M), including NOVEC HFE 7500 Engineered Fluid.

Droplet—a small volume of a first liquid that is encapsulated by an immiscible second liquid, such as a continuous phase of an emulsion (and/or by a larger droplet). The volume of a droplet, and/or the average volume of droplets in an emulsion, may, for example, be less than about one microliter (or between about one microliter and one nanoliter or between about one microliter and one picoliter), less than about one nanoliter (or between about one nanoliter and one picoliter), or less than about one picoliter (or between about one picoliter and one femtoliter), among others. A droplet (or droplets of an emulsion) may have a diameter (or an average diameter) of less than about 1000, 100, or 10 micrometers, or about 1000 to 10 micrometers, among others. A droplet may be spherical or nonspherical. A droplet may be a simple droplet or a compound droplet.

Compound droplet—a droplet in which at least one droplet encloses at least one other droplet. A compound droplet includes at least two immiscible liquids, with one of the liquids surrounding the other liquid in the compound droplet to form at least one droplet within a droplet. A droplet that is surrounded by another droplet may be described as an inner droplet, which may or may not be the innermost droplet of a compound droplet. A droplet enclosing another droplet may be described as an outer droplet, which may or may not be the outermost droplet of a compound droplet. In contrast to a compound droplet, a simple droplet is not surrounded by another droplet.

Multiple emulsion—an emulsion including compound droplets. A multiple emulsion can be characterized according to the level of encapsulation of its constituent compound droplets, with a higher-order emulsion having more levels of encapsulation than a lower-order emulsion. For example, a double emulsion contains compound droplets structured as one more droplets within an enclosing droplet, a triple emulsion contains compound droplets structured as a droplet within a droplet within a droplet, and so on. In contrast, a single emulsion contains simple droplets in a continuous phase.

Surfactant—a surface-active substance capable of reducing the surface tension of a liquid in which it is present. A surfactant, which also or alternatively may be described as a detergent and/or a wetting agent, may incorporate both a hydrophilic portion and a hydrophobic portion, which may collectively confer a dual hydrophilic-hydrophobic character on the surfactant. A surfactant may, in some cases, be characterized according to its hydrophilicity relative to its hydrophobicity. Each dispersed and/or continuous phase may incorporate at least one surfactant. Each aqueous phase may include at least one nonionic surfactant and/or ionic surfactant. In some embodiments, the aqueous phase may include a surfactant that is a block copolymer of polypropylene oxide and polyethylene oxide. More particularly, the surfactant may be a block copolymer of polypropylene oxide and polyethylene oxide sold under the trade names PLURONIC and TETRONIC (BASF). In some embodiments, the surfactant may be a nonionic block copolymer of polypropylene oxide and polyethylene oxide sold under the trade name PLURONIC F-68. In some embodiments, the surfactant of the aqueous phase may be a water-soluble and/or hydrophilic fluorosurfactant. Exemplary fluorosurfactants for the aqueous phase are sold under the trade name ZONYL (DuPont), such as ZONYL FSN fluorosurfactants. In some cases, the surfactant may include polysorbate 20 (sold under the trade name TWEEN-20 by ICI Americas, Inc.). The concentration of a particular surfactant or total surfactant present in the aqueous phase and oil phase may be selected to stabilize compound droplets until they are heated to a desired fusion temperature. An exemplary concentration of surfactant for the aqueous phase is about 0.01 to 10%, 0.05 to 5%, 0.1 to 1%, or 0.5% by weight, among others.

A nonaqueous or oil phase may incorporate a hydrophobic surfactant. The nonaqueous phase may include one or more surfactants. The surfactants may include a nonionic surfactant, an ionic surfactant (a cationic (positively-charged) or anionic (negatively-charged) surfactant), or both types of surfactant. Exemplary anionic surfactants that may be suitable include carboxylates, sulphonates, phosphonates, and so on. The one or more surfactants may be present, individually or collectively, at any suitable concentration, such as greater than about 0.001% or 0.01%, or about 0.001% to 10%, 0.05% to 2%, or 0.05% to 0.5%, among others.

The one or more surfactants present in the nonaqueous phase (or oil phase) may be fluorinated surfactants (e.g., surfactant compounds that are polyfluorinated and/or perfluorinated). Exemplary fluorinated surfactants are fluorinated polyethers, such as carboxylic acid-terminated perfluoropolyethers, carboxylate salts of perfluoropolyethers, and/or amide or ester derivatives of carboxylic acid-terminated perfluoropolyethers. Exemplary but not exclusive perfluoropolyethers are commercially available under the trade name KRYTOX (DuPont), such as KRYTOX-FSH, the ammonium salt of KRYTOX-FSH ("KRYTOX-AS"), or a morpholino derivative of KRYTOX-FSH ("KRYTOX-M"), among others. Other fluorinated polyethers that may be suitable include at least one polyethylene glycol (PEG) moiety.

Fluorinated—including fluorine, typically substituted for hydrogen. Any of the fluorinated compounds disclosed herein may be polyfluorinated, meaning that such compounds each include many fluorines, such as more than five or ten fluorines, among others. Any of the fluorinated compounds disclosed herein also or alternatively may be perfluorinated, meaning that most or all hydrogens have been replaced with fluorine.

Sample—a compound, composition, and/or mixture of interest, from any suitable source(s). A sample is the general subject of interest for a test that analyzes an aspect of the sample, such as an aspect related to at least one analyte that may be present in the sample. Samples may be analyzed in their natural state, as collected, and/or in an altered state, for example, following storage, preservation, extraction, lysis, dilution, concentration, purification, filtration, mixing with one or more reagents, pre-amplification (e.g., to achieve target enrichment by performing limited cycles (e.g., <15) of PCR on sample prior to PCR), removal of amplicon (e.g., treatment with uracil-d-glycosylase (UDG) prior to PCR to eliminate any carry-over contamination by a previously generated amplicon (i.e., the amplicon is digestable with UDG because it is generated with dUTP instead of dTTP)), partitioning, or any combination thereof, among others. Clinical samples may include nasopharyngeal wash, blood, plasma, cell-free plasma, buffy coat, saliva, urine, stool, sputum, mucous, wound swab, tissue biopsy, milk, a fluid aspirate, a swab (e.g., a nasopharyngeal swab), and/or tissue, among others. Environmental samples may include water, soil, aerosol, and/or air, among others. Research samples may include cultured cells, primary cells, bacteria, spores, viruses, small organisms, any of the clinical samples listed above, or the like. Additional samples may include foodstuffs, weapons components, biodefense samples to be tested for bio-threat agents, suspected contaminants, and so on.

Samples may be collected for diagnostic purposes (e.g., the quantitative measurement of a clinical analyte such as an infectious agent) or for monitoring purposes (e.g., to determine that an environmental analyte of interest such as a biothreat agent has exceeded a predetermined threshold).

Reagent—a compound, set of compounds, and/or composition that is combined with a sample in order to perform a particular test(s) on the sample. A reagent may be a target-specific reagent, which is any reagent composition that confers specificity for detection of a particular target(s) or analyte(s) in a test. A reagent optionally may include a chemical reactant and/or a binding partner for the test. A reagent may, for example, include at least one nucleic acid, protein (e.g., an enzyme), cell, virus, organelle, macromolecular assembly, potential drug, lipid, carbohydrate, inorganic substance, or any combination thereof, and may be an aqueous composition, among others. In exemplary embodiments, the reagent may be an amplification reagent, which may include at least one primer or at least one pair of primers for amplification of a nucleic acid target, at least one probe and/or dye to enable detection of amplification, a polymerase, a ligase, nucleotides (dNTPs and/or NTPs), divalent magnesium ions, or any combination thereof, among others. In some embodiments, the reagent may be a PCR reagent, namely, a reagent involved in PCR amplification, such as a primer, a heat-stable polymerase, at least one nucleotide (dNTP or NTP), or magnesium, among others. An amplification reagent and/or a nucleic acid target each may be described as a reaction component.

The amplification reagent may be present at an effective amount, namely, an amount sufficient to enable amplification of a nucleic acid target in the presence of other necessary reagents. Exemplary effective amounts of PCR reagents are as follows: heat-stable DNA polymerase, 0.005 to 0.5 Units/µL; dNTPs, 50 µM to 5 mM each; primers, 0.02 to 5.0 µM each; and $Mg^{2+}$, 0.5 to 10 mM.

Nucleic acid—a compound comprising a chain of nucleotide monomers. A nucleic acid may be single-stranded or double-stranded (i.e., base-paired with another nucleic acid), among others. The chain of a nucleic acid may be composed of any suitable number of monomers, such as at least about ten or one-hundred, among others. Generally, the length of a nucleic acid chain corresponds to its source, with synthetic nucleic acids (e.g., primers and probes) typically being shorter, and biologically/enzymatically generated nucleic acids (e.g., nucleic acid analytes) typically being longer.

A nucleic acid may have a natural or artificial structure, or a combination thereof. Nucleic acids with a natural structure, namely, deoxyribonucleic acid (DNA) and ribonucleic acid (RNA), generally have a backbone of alternating pentose sugar groups and phosphate groups. Each pentose group is linked to a nucleobase (e.g., a purine (such as adenine (A) or guanine (T)) or a pyrimidine (such as cytosine (C), thymine (T), or uracil (U))). Nucleic acids with an artificial structure are analogs of natural nucleic acids and may, for example, be created by changes to the pentose and/or phosphate groups of the natural backbone. Exemplary artificial nucleic acids include glycol nucleic acids (GNA), peptide nucleic acids (PNA), locked nucleic acid (LNA), threose nucleic acids (TNA), and the like.

The sequence of a nucleic acid is defined by the order in which nucleobases are arranged along the backbone. This sequence generally determines the ability of the nucleic acid to bind specifically to a partner chain (or to form an intramolecular duplex) by hydrogen bonding. In particular, adenine pairs with thymine (or uracil) and guanine pairs with cytosine. A nucleic acid that can bind to another nucleic acid in an antiparallel fashion by forming a consecutive string of such base pairs with the other nucleic acid is termed "complementary."

Replication—a process forming a copy (i.e., a direct copy and/or a complementary copy) of a nucleic acid or a segment thereof. Replication generally involves an enzyme, such as a polymerase and/or a ligase, among others. The nucleic acid and/or segment replicated is a template (and/or a target) for replication.

Amplification—a reaction in which replication occurs repeatedly over time to form multiple copies of at least one segment of a template molecule. Amplification may generate an exponential or linear increase in the number of copies as amplification proceeds. Typical amplifications produce a greater than 1,000-fold increase in copy number and/or signal. Exemplary amplification reactions for the assays disclosed herein may include the polymerase chain reaction (PCR) or ligase chain reaction (LCR), each of which is driven by thermal cycling. Thermal cycling generally involves cycles of heating and cooling a reaction mixture to perform successive rounds of denaturation (melting), annealing, and extension. The assays also or alternatively may use other amplification reactions, which may be performed isothermally, such as branched-probe DNA assays, cascade-RCA, helicase-dependent amplification, loop-mediated isothermal amplification (LAMP), nucleic acid based amplification (NASBA), nicking enzyme amplification reaction (NEAR), PAN-AC, Q-beta replicase amplification, rolling circle replication (RCA), self-sustaining sequence replication, strand-displacement amplification, and the like. Amplification may utilize a linear or circular template.

Amplification may be performed with any suitable reagents. Amplification may be performed, or tested for its occurrence, in an amplification mixture, which is any composition capable of generating multiple copies of a nucleic acid target molecule, if present, in the composition. An amplification mixture may include any combination of at least one primer or primer pair, at least one probe, at least one replication enzyme (e.g., at least one polymerase, such as at least one DNA and/or RNA polymerase, and/or at least one ligase), and/or deoxynucleotide (and/or nucleotide) triphosphates (dNTPs and/or NTPs), among others.

Hot-start amplification—amplification in which reaction (e.g., polymerization and/or ligation) does not occur significantly until an elevated temperature is reached. The elevated temperature may be at least about the annealing temperature for amplification, to reduce non-target amplification.

PCR—nucleic acid amplification that relies on alternating cycles of heating and cooling (i.e., thermal cycling) to achieve successive rounds of replication. PCR may be performed by thermal cycling between two or more temperature set points, such as a higher melting (denaturation) temperature and a lower annealing/extension temperature, or among three or more temperature set points, such as a higher melting temperature, a lower annealing temperature, and an intermediate extension temperature, among others. PCR may be performed with a heat-stable polymerase, such as Taq DNA polymerase (e.g., wild-type enzyme, a Stoffel fragment, Fast-Start polymerase, etc.), Pfu DNA polymerase, S-Tbr polymerase, Tth polymerase, Vent polymerase, or a combination thereof, among others. PCR generally produces an exponential increase in the amount of a product amplicon over successive cycles.

Any suitable PCR methodology or combination of methodologies may be utilized in the assays disclosed herein, such as allele-specific PCR, assembly PCR, asymmetric PCR, digital PCR, endpoint PCR, hot-start PCR, in situ PCR, intersequence-specific PCR, inverse PCR, linear after exponential PCR, ligation-mediated PCR, methylation-specific PCR, miniprimer PCR, multiplex ligation-dependent probe amplification, multiplex PCR, nested PCR, overlap-extension PCR, polymerase cycling assembly, qualitative PCR, quantitative PCR, real-time PCR, RT-PCR, single-cell PCR, solid-phase PCR, thermal asymmetric interlaced PCR, touchdown PCR, universal fast walking PCR, or any combination thereof, among others.

Amplicon—a product of an amplification reaction. An amplicon may be single-stranded or double-stranded, or a combination thereof. An amplicon corresponds to any suitable segment or the entire length of a nucleic acid target.

Primer—a nucleic acid capable of, and/or used for, priming replication of a nucleic acid template. Thus, a primer is a shorter nucleic acid that is complementary to a longer template. During replication, the primer may be extended, based on the template sequence, to produce a longer nucleic acid that is a complementary copy of the template. Extension may occur by successive addition of individual nucleotides (e.g., by the action of a polymerase) or by attachment of a block of nucleotides (e.g., by the action of a ligase joining a pair of primers), among others. A primer may be DNA, RNA, an analog thereof (i.e., an artificial nucleic acid), or any combination thereof. A primer may have any suitable length, such as at least about 10, 15, 20, or 30 nucleotides. Exemplary primers are synthesized chemically. Primers may be supplied as at least one pair of primers for amplification of at least one nucleic acid target. A pair of primers may be a sense primer and an antisense primer that collectively define the opposing ends (and thus the length) of a resulting amplicon.

Probe—a nucleic acid connected to at least one label, such as at least one dye. A probe may be a sequence-specific binding partner for a nucleic acid target and/or amplicon. The probe may be designed to enable detection of target amplification based on fluorescence resonance energy transfer (FRET). An exemplary probe for the nucleic acid assays disclosed herein includes one or more nucleic acids connected to a pair of dyes that collectively exhibit fluorescence resonance energy transfer (FRET) when proximate one another. The pair of dyes may provide first and second emitters, or an emitter and a quencher, among others. Fluorescence emission from the pair of dyes changes when the dyes are separated from one another, such as by cleavage of the probe during primer extension (e.g., a 5' nuclease assay, such as with a TAQMAN probe), or when the probe hybridizes to an amplicon (e.g., a molecular beacon probe). The nucleic acid portion of the probe may have any suitable structure or origin, for example, the portion may be a locked nucleic acid, a member of a universal probe library, or the like. In other cases, a probe and one of the primers of a primer pair may be combined in the same molecule (e.g., AMPLIFLUOR primers or SCORPION primers). As an example, the primer-probe molecule may include a primer sequence at its 3' end and a molecular beacon-style probe at its 5' end. With this arrangement, related primer-probe molecules labeled with different dyes can be used in a multiplexed assay with the same reverse primer to quantify target sequences differing by a single nucleotide (single nucleotide polymorphisms (SNPs)). Another exemplary probe for droplet-based nucleic acid assays is a Plexor primer.

Label—an identifying and/or distinguishing marker or identifier connected to or incorporated into any entity, such as a compound, biological particle (e.g., a cell, bacteria, spore, virus, or organelle), or droplet. A label may, for example, be a dye that renders an entity optically detectable and/or optically distinguishable. Exemplary dyes used for labeling are fluorescent dyes (fluorophores) and fluorescence quenchers.

Reporter—a compound or set of compounds that reports a condition, such as the extent of a reaction. Exemplary reporters comprise at least one dye, such as a fluorescent dye or an energy transfer pair, and/or at least one oligonucleotide. Exemplary reporters for nucleic acid amplification assays may include a probe and/or an intercalating dye (e.g., SYBR Green, ethidium bromide, etc.).

Binding partner—a member of a pair of members that bind to one another. Each member may be a compound or biological particle (e.g., a cell, bacteria, spore, virus, organelle, or the like), among others. Binding partners may bind specifically to one another. Specific binding may be characterized by a dissociation constant of less than about $10^{-4}$, $10^{-6}$, $10^{-8}$, or $10^{-10}$ M, among others. Exemplary specific binding partners include biotin and avidin/streptavidin, a sense nucleic acid and a complementary antisense nucleic acid (e.g., a probe and an amplicon), a primer and its target, an antibody and a corresponding antigen, a receptor and its ligand, and the like.

II. Exemplary Fusion of a Multiple Emulsion

FIG. 1 shows a schematic flow diagram illustrating an exemplary multiple emulsion 20 that is heated, indicated at 22, to promote fusion of compound droplets 24 with an aqueous continuous phase 26. Multiple emulsion 20 may, for example, be a water-in-oil-in-water (W/O/W) emulsion that is converted, at least partially, to an oil-in-water (O/W) emulsion by heat.

Each compound droplet 24 may include an outer droplet 28, which may be an oil droplet. The outer droplet may enclose at least one inner droplet 30, which may be an aqueous droplet. The outer droplet may enclose any suitable number of inner droplets, such as one to up to 10,000, or more. In any event, inner droplet 30 may be miscible with continuous phase 26 but may be prevented from merging with the continuous phase by the oil layer provided by outer droplet 28. The terms "merge," "coalesce," and "fuse" are intended to be synonyms for the process of joining separate fluid phases, such as an aqueous droplet with a surrounding aqueous phase.

Aqueous droplet 30 may contain at least one amplification reagent 32, which is indicated schematically in FIG. 1 by an asterisk ("*"). Continuous phase 26 may be deficient for the amplification reagent before heating. In other words, the reagent may be absent from continuous phase 26 or present substantially below the effective amount for amplification. Accordingly, the continuous phase, before heating, may provide a deficient or incomplete reaction mixture 34 for amplification, which is not capable of efficient amplification of a nucleic acid target, if present, in the deficient/incomplete reaction mixture. However, inner droplets 30 may be designed to complement the amplification reagents present in the continuous phase, such that fusion of inner droplets 30 with continuous phase 26 forms a complete reaction mixture 36 capable of amplification of the nucleic acid target, if present, with proper thermal cycling.

Further aspects of forming emulsions and fusing fluid phases are described in the references listed above under Cross-References, particularly U.S. patent application Ser. No. 12/586,626, filed Sep. 23, 2009; U.S. patent application Ser. No. 12/862,542, filed Aug. 24, 2010; and U.S. patent application Ser. No. 12/976,827, filed Dec. 22, 2010; which are incorporated herein by reference.

III. Exemplary Method of Sample Analysis Using a Multiple Emulsion

FIG. 2 shows a flowchart 50 presenting an exemplary method of sample analysis using a multiple emulsion to controllably combine amplification reagents. The steps shown in FIG. 2 may be performed in any suitable order and combination and may be combined with any other steps or aspects disclosed elsewhere herein or in the references listed above under Cross-References, which are incorporated herein by reference.

A multiple emulsion may be provided, indicated at 52. The multiple emulsion may include compound droplets disposed in an aqueous phase that is continuous or dispersed. Each compound droplet may include an oil droplet enclosing at least one aqueous droplet, which may contain at least one amplification reagent, such as a heat-stable polymerase, a heat-stable ligase, one or more deoxynucleotide triphosphates, magnesium, one or more primers, or any combination thereof, among others. The amplification reagent is sequestered in an aqueous portion of the compound droplets and cannot react (e.g., cannot enable polymerization or ligation in the surrounding aqueous phase until released). The amplification reagent may be present in sufficient quantity to supply an effective amount of the reagent to the surrounding aqueous phase.

The multiple emulsion may be a segregated reaction mixture. The surrounding aqueous phase may provide an incomplete reaction mixture that contains an effective amount of each reaction component for an amplification reaction, except the reagent(s) contained in the compound droplet. The incomplete reaction mixture also may contain a sample to be tested for a target nucleic acid, or the sample may be added later, as described below.

The multiple emulsion may be formed from another emulsion composition that contains the compound droplets. The emulsion composition may be combined with other reaction components for amplification of a target to generate the multiple emulsion. For example, the other reaction components may be contacted with an aqueous continuous phase of the emulsion composition to create the incomplete reaction mixture surrounding the compound droplets.

In some embodiments, a master mix for amplification may be formed with the compound droplets and other reaction components. The master mix may include the compound droplets and a continuous phase that collectively contain all of the reagents necessary to perform amplification of a nucleic acid target, if combined with a suitable volume of the master mix. The master mix also may or may not contain reagents for reverse transcription, to permit RT-PCR analysis of samples. Portions of the master mix may be dispensed to a plurality of containers, such as to individual vials or to wells of a PCR plate, among others. The master mix may be dispensed with any suitable fluid transfer device, such as a pipette. At least one sample also may be dispensed to each container to form a segregated reaction mixture in the form of a multiple emulsion in each container.

The multiple emulsion may be heated, indicated at 54, to fuse aqueous droplets of the compound droplets with the surrounding aqueous phase, to create a reaction mixture. In some embodiments, heating may be provided as the temperature is increased for the initial melting step of an amplification reaction (e.g., PCR). In any event, heating destabilizes the emulsion and particularly an oil layer between the aqueous droplets and the continuous phase.

The reaction mixture may be cycled thermally, indicated at 56, to promote amplification of one or more nucleic acid targets.

A signal may be detected, indicated at 58, from the reaction mixture before, during, and/or after thermal cycling, to determine whether (and/or how much) amplification occurred in the mixture. Alternatively, or in addition, the amplified target may be isolated from the reaction mixture.

Further aspects of forming compound droplets, heating compound droplets to induce fusion, thermal cycling, signal detection, and data analysis are described in the references listed above under Cross-References, which are incorporated herein by reference, particularly U.S. patent application Ser. No. 12/586,626, filed Sep. 23, 2009; U.S. patent application Ser. No. 12/862,542, filed Aug. 24, 2010; and U.S. patent application Ser. No. 12/976,827, filed Dec. 22, 2010.

IV. Exemplary System for Forming Compound Droplets

FIG. 3 shows a schematic view of an exemplary system 70 for forming compound droplets 24 containing at least one reagent 32, for the multiple emulsion of FIG. 1. System 70 includes channels 71 that carry fluid to a serial arrangement of droplet generators formed where the channels intersect.

Reagent 32 may be part of an aqueous composition 72 ("water+reagent") that forms aqueous inner droplets 30 of compound droplets 24. In addition to reagent(s) 32, composition 72 may include at least one surfactant, a buffer, glycerol, salt, and/or the like. In some embodiments, the reagent may be or include a heat-stable polymerase or ligase. The polymerase may be recombinant or native Taq polymerase in an active configuration (i.e., the enzyme does not require heat activation if all required reaction components are available), or may be in an inactive configuration until heated.

During system operation, aqueous composition 72 may flow to a first droplet generator 74, where inner droplets 30 are formed as partitions of composition 72 enclosed by an oil phase 76. The oil phase may contain an oil 78 and at least one surfactant 80. For example, the oil phase may include a fluorinated oil and at least one fluorinated surfactant. In any event, the surfactant may be a biocompatible surfactant that facilitates generation of an emulsion that is stable at temperatures less than about 40° C., 50° C., 60° C., 70° C. or 80° C., among others, but unstable at temperatures greater than about 50° C., 60° C., 70° C., 80° C., or 90° C., among others. Also, the walls of the channel downstream of droplet generator 74, and upstream of the next droplet generator, may be hydrophobic to restrict wetting the walls with aqueous droplets 30.

The aqueous droplets in oil phase 76 may flow to a second droplet generator 82, where compound droplets 24 are formed in an aqueous continuous phase 84. The continuous phase may contain at least one surfactant, which may be the same as or a different surfactant from that present in aqueous droplets 30, and at the same or a different concentration. Also, the walls downstream of droplet generator 82 may be hydrophilic to restrict wetting of the walls with outer oil droplets 28 of compound droplets 24.

V. Exemplary Fusion within Compound Droplets

FIG. 4 shows a schematic flow diagram illustrating an exemplary multiple emulsion 100 that is heated to promote fusion within compound droplets 102. Emulsion 100 may be a water-in-oil-in-water-in-oil (W/O/W/O) emulsion that corresponds to emulsion 20 of FIG. 1, but in a partitioned configuration that disperses aqueous phase 26 (and enclosed compound droplets 24) in an immiscible continuous phase 104.

Compound droplets 102 each may be composed of at least three types of droplets: one or more inner aqueous droplets 30 enclosed by one or more oil droplets 28, which in turn are enclosed by an outer aqueous droplet 108 (composed of aqueous phase 26 of FIG. 1, but dispersed). Each inner droplet 30 may contain at least one amplification reagent 32. The compound droplets may be disposed in continuous phase 104, such as an oil phase including an oil and at least one surfactant.

Each compound droplet, and particularly inner droplets 30 and outer droplet 108 collectively, may provide an effective amount of each reaction component necessary to perform amplification of a nucleic acid target, if present in one of the aqueous phases of the compound droplet. However, at least one of the reaction components may be separated from the other reaction components by a layer of oil provided by oil droplets 28, to prevent reaction before heat-induced fusion. Accordingly, fusion of inner droplets 30 with outer droplet 108, in response to heat, may form an oil-in-water-in-oil (O/W/O) emulsion 112 that contains a complete reaction mixture 114 for amplification of a target in each outer droplet 108.

VI. Exemplary System for Forming Compound Droplets that Fuse Internally

FIG. 5 shows a schematic view of an exemplary system 120 for forming multiple emulsion 100 of FIG. 4. A W/O/W emulsion (e.g., emulsion 20 of FIG. 1) and an oil phase 122 may feed a droplet generator 124 to form compound droplets 102 of multiple emulsion 100. Droplet generator 124 may be structured generally as described for first droplet generator 74 of FIG. 3. Any number of inner droplets 30 may be disposed in each outer droplet 108, such as 1 to 10,000, among others.

Heating emulsion 100 may produce O/W/O emulsion 112 (see Section V and FIG. 4), which releases the amplification reagent(s) (e.g., Taq DNA polymerase) and/or sample from the inner droplets.

VII. Selected Embodiments

This section presents selected embodiments of the present disclosure related to methods and compositions for coalescence of a continuous phase with inner droplets of compound droplets to form a reaction mixture.

1. A method of PCR amplification, comprising: (A) providing a multiple emulsion including compound droplets disposed in a continuous aqueous phase, each compound droplet including an oil droplet enclosing at least one aqueous droplet, the aqueous droplet containing at least one PCR reagent; (B) heating the multiple emulsion such that aqueous droplets of the compound droplets fuse with the continuous phase to supply an effective amount of the PCR reagent to the continuous phase, to form a reaction mixture capable of PCR amplification of a nucleic acid target, if present, in the reaction mixture; and (C) cycling the reaction mixture thermally to promote PCR amplification.

2. The method of paragraph 1, wherein the step of providing includes a step of providing a multiple emulsion having a continuous phase that lacks the PCR reagent.

3. The method of paragraph 1, further comprising a step of detecting one or more signals corresponding to PCR amplification of the nucleic acid target in the reaction mixture.

4. The method of paragraph 1, wherein the step of providing includes a step of providing a multiple emulsion containing a DNA polymerase in the at least one aqueous droplet.

5. The method of paragraph 4, wherein the step of providing includes a step of providing a multiple emulsion containing Taq DNA polymerase in the at least one aqueous droplet.

6. The method of paragraph 1, wherein the step of providing includes a step of providing a multiple emulsion in which the PCR reagent contained by the at least one aqueous droplet is magnesium, at least one deoxyribonucleotide triphosphate, at least one nucleic acid primer, or a combination thereof.

7. The method of paragraph 1, wherein the step of providing a multiple emulsion includes a step of combining (a) a composition including the compound droplets and (b) an effective amount of each reaction component for the PCR amplification except the at least one PCR reagent.

8. The method of paragraph 1, wherein the step of providing includes a step of forming a composition comprising (a) a continuous phase including an effective amount of each reaction component for the PCR amplification except the at least one PCR reagent and the nucleic acid target and (b) a plurality of compound droplets containing the at least one PCR reagent, and a step of combining at least a volume portion of the composition and a sample that provides the nucleic acid target, if present, in the reaction mixture.

9. The method of paragraph 8, wherein the composition is a PCR master mix, and wherein the step of combining includes a step of dispensing volume portions of the PCR master mix and at least one sample to each of a plurality of containers.

10. The method of paragraph 1, wherein the step of providing a multiple emulsion includes a step of providing a multiple emulsion in which fusion of the at least one aqueous droplet with the continuous phase does not occur substantially until the multiple emulsion is heated to a temperature of at least 50° C.

11. A method of PCR amplification, comprising: (A) providing a first composition including compound droplets disposed in a continuous aqueous phase, each compound droplet including an oil droplet enclosing at least one aqueous droplet, the aqueous droplet containing a heat-stable DNA polymerase; (B) forming a second composition by combining the continuous aqueous phase with other reaction components for PCR amplification of a nucleic acid target, if present, in the second composition; (C) heating the second composition such that aqueous droplets of the compound droplets fuse with the continuous aqueous phase to supply an effective amount of the PCR reagent to the continuous phase, to form a reaction mixture capable of PCR amplification of a nucleic acid target, if present, in the reaction mixture; and (D) cycling the reaction mixture thermally to promote PCR amplification.

12. A composition for PCR amplification, comprising a multiple emulsion including compound droplets disposed in a continuous aqueous phase, each compound droplet including an oil droplet enclosing at least one aqueous droplet, the aqueous droplet containing at least one PCR reagent, wherein heating the composition causes aqueous droplets of the compound droplets to fuse with the continuous phase to supply an effective amount of the PCR reagent to the continuous phase, to form a reaction mixture capable of PCR amplification of a nucleic acid target, if present, in the reaction mixture.

13. The composition of paragraph 12, wherein the at least one aqueous droplet contains a heat-stable DNA polymerase.

14. A composition for use in PCR amplification, comprising a multiple emulsion including compound droplets disposed in a continuous aqueous phase, each compound droplet including an oil droplet enclosing at least one aqueous droplet, the aqueous droplet containing a heat-stable DNA polymerase.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

The invention claimed is:

1. A method of nucleic acid amplification, comprising providing a composition comprising a plurality of compound droplets disposed in an aqueous phase, wherein each compound droplet comprise a plurality of aqueous droplets, each aqueous droplet enclosed by an oil droplet and each aqueous droplet containing at least one amplification reagent;
heating the composition to cause fusion of the aqueous droplets with the aqueous phase, such that the at least one amplification reagent is added to the aqueous phase to form at least one reaction mixture; and cycling the at least one reaction mixture thermally to encourage amplification of a nucleic acid target.

2. The method of claim 1, further comprising a step of detecting one or more signals corresponding to amplification of the nucleic acid target in the at least one reaction mixture.

3. The method of claim 1, wherein the aqueous droplets contain DNA polymerase.

4. The method of claim 3, wherein the DNA polymerase is a Taq DNA polymerase.

5. The method of claim 1, wherein the at least one amplification reagent includes magnesium, at least one deoxynucleotide triphosphate, at least one primer, or a combination thereof.

6. The method of claim 1, wherein the aqueous phase is continuous.

7. The method of claim 1, wherein the aqueous phase is dispersed.

8. The method of claim 1,
wherein the aqueous phase lacks an effective amount of at least one PCR reagent that is contained by the aqueous droplets, wherein;
the at least one reaction mixture is capable of PCR amplification of a nucleic acid target, if present, in the reaction mixture, and
wherein cycling the at least one reaction mixture thermally encourages PCR amplification of the nucleic acid target.

9. The method of claim 1, wherein fusion of the aqueous droplets with the aqueous phase occurs at least predominantly after the composition has been heated to a temperature of at least about 50° C.

10. The method of claim 8, wherein the aqueous phase in the composition provided includes an effective amount of each reaction component for the PCR amplification except the at least one PCR reagent.

11. A method of nucleic acid amplification, comprising providing a composition comprising a plurality of compound droplets disposed in an aqueous phase, wherein each compound droplet comprise a plurality of aqueous droplets, each aqueous droplet enclosed by an oil droplet and each aqueous droplet containing a heat stable polymerase;
heating the composition such that the aqueous droplets with the aqueous phase, to form at least one reaction mixture capable of PCR amplification of a nucleic acid target, if present, in the at least one reaction mixture; and cycling the at least one reaction mixture thermally to encourage PCR amplification.

12. A composition for nucleic acid amplification, comprising an aqueous phase that is dispersed or continuous; a plurality of compound droplet disposed in the aqueous phase; wherein each compound droplet comprise a plurality of aqueous droplets, each aqueous droplet enclosed by an oil droplet and each aqueous droplet containing at least one amplification reagent, wherein heating the composition causes the aqueous droplets to fuse with the aqueous phase to supply the at least one amplification reagent to the aqueous phase.

13. The composition of claim 12, wherein the aqueous droplets contains a heat-stable DNA polymerase.

14. The composition of claim 12, where heating the composition forms at least one reaction mixture capable of amplification of a nucleic acid target, if present, in the reaction mixture.

* * * * *